United States Patent
Li et al.

(10) Patent No.: US 10,093,717 B2
(45) Date of Patent: Oct. 9, 2018

(54) CHIMERIC ANTIGEN RECEPTOR CONTAINING A TOLL-LIKE RECEPTOR INTRACELLULAR DOMAIN

(71) Applicant: SHENZHEN IN VIVO BIOMEDICINE TECHNOLOGY LIMITED COMPANY, Shenzhen, Guangdong (CN)

(72) Inventors: Peng Li, Shenzhen (CN); Yunxin Lai, Shenzhen (CN); Simiao Lin, Shenzhen (CN); Yao Yao, Shenzhen (CN)

(73) Assignee: SHENZHEN IN VIVO BIOMEDICINE TECHNOLOGY LIMITED COMPANY, Shenzhen (CN)

( * ) Notice: Subject to any disclaimer, the term of this patent is extended or adjusted under 35 U.S.C. 154(b) by 44 days.

(21) Appl. No.: 15/112,619

(22) PCT Filed: Aug. 7, 2015

(86) PCT No.: PCT/CN2015/086352
§ 371 (c)(1),
(2) Date: Jul. 19, 2016

(87) PCT Pub. No.: WO2017/024440
PCT Pub. Date: Feb. 16, 2017

(65) Prior Publication Data
US 2017/0233454 A1    Aug. 17, 2017

(51) Int. Cl.
| | | |
|---|---|---|
| C07K 14/705 | (2006.01) |
| C07K 16/30 | (2006.01) |
| C07K 14/715 | (2006.01) |
| C07K 19/00 | (2006.01) |
| C12N 15/62 | (2006.01) |
| C12N 15/63 | (2006.01) |
| C07K 14/725 | (2006.01) |
| C07K 16/28 | (2006.01) |
| A61K 39/00 | (2006.01) |

(52) U.S. Cl.
CPC ........ *C07K 14/7155* (2013.01); *C07K 14/705* (2013.01); *C07K 14/7051* (2013.01); *C07K 14/70521* (2013.01); *C07K 16/2803* (2013.01); *C07K 16/30* (2013.01); *C07K 19/00* (2013.01); *C12N 15/62* (2013.01); *C12N 15/63* (2013.01); *A61K 2039/505* (2013.01); *C07K 2317/622* (2013.01); *C07K 2317/73* (2013.01); *C07K 2319/03* (2013.01); *C07K 2319/30* (2013.01)

(58) Field of Classification Search
CPC ............ C07K 14/7051; C07K 14/7155; C07K 14/70521; C07K 16/2803; C07K 2317/622; C07K 2319/00–2319/74; A61K 2039/505; C12N 2510/00
See application file for complete search history.

(56) References Cited

U.S. PATENT DOCUMENTS

2016/0075755 A1* 3/2016 Valdes .................. C07K 14/71
424/185.1

FOREIGN PATENT DOCUMENTS

| CN | 104087607 A | 10/2014 |
| WO | WO-2014172584 A1 | 10/2014 |

OTHER PUBLICATIONS

Cartellieri et al., J. Biomed. Biotech., pp. 1-13; doi:10.1155/2010/956304 (Year: 2010).*
Lai et al., Leukemia, 1-8; doi:10.1038/leu.2017.249 (Year: 2017).*
Guan et al., J. Immunol., 184:5094-5103 (Year: 2010).*
Kowolik et al., Cancer Res. 66:10995-11004 (Year: 2006).*
Mercier et al., J. Immunol. 182:1860-67 (Year: 2009).*

* cited by examiner

*Primary Examiner* — Jessica H Roark
(74) *Attorney, Agent, or Firm* — McCarter & English, LLP; Steven G. Davis; Wei Song

(57) ABSTRACT

The present invention relates to a chimeric antigen receptor, a nucleic acid encoding the same and a cell expressing the same, and their use in manufacturing drugs for treating tumors. The chimeric antigen receptor of the present invention is characterized by its intracellular domain including at least Toll-like receptor 1 and/or Toll-like receptor 2 intracellular domain(s); compared to the prior art, the chimeric antigen receptors of the present invention has significant advantages in T cell expansion, cytotoxicity, T cell invasion and migration, eliminating immunosuppressive effect of regulatory T cells and promoting the formation of memory T cells, etc.

13 Claims, 11 Drawing Sheets
Specification includes a Sequence Listing.

SEQUENCE LISTING

```
<160> NUMBER OF SEQ ID NOS: 17

<210> SEQ ID NO 1
<211> LENGTH: 1487
<212> TYPE: DNA
<213> ORGANISM: Artificial sequence
<220> FEATURE:
<223> OTHER INFORMATION: CAR19

<400> SEQUENCE: 1
gtttaaacga attcatgctt ctcctggtga caagccttct gctctgtgag ttaccacacc      60
cagcattcct cctgatccca gacatccaga tgacacagac tacatcctcc ctgtctgcct     120
ctctgggaga cagagtcacc atcagttgca gggcaagtca ggacattagt aaatatttaa     180
attggtatca gcagaaacca gatggaactg ttaaactcct gatctaccat acatcaagat     240
tacactcagg agtcccatca aggttcagtg gcagtgggtc tggaacagat tattctctca     300
ccattagcaa cctggagcaa gaagatattg ccacttactt ttgccaacag ggtaatacgc     360
ttccgtacac gttcggaggg gggactaagt tggaaataac aggctccacc tctggatccg     420
gcaagcccgg atctggcgag ggatccacca agggcgaggt gaaactgcag gagtcaggac     480
ctggcctggt ggcgccctca cagagcctgt ccgtcacatg cactgtctca ggggtctcat     540
tacccgacta tggtgtaagc tggattcgcc agcctccacg aaagggtctg gagtggctgg     600
gagtaatatg gggtagtgaa accacatact ataattcagc tctcaaatcc agactgacca     660
tcatcaagga caactccaag agccaagttt tcttaaaaat gaacagtctg caaactgatg     720
acacagccat ttactactgt gccaaacatt attactacgg tggtagctat gctatggact     780
actggggtca aggaacctca gtcaccgtct cctcagcggc cgcaattgaa gttatgtatc     840
ctcctcctta cctagacaat gagaagagca atggaaccat tatccatgtg aaagggaaac     900
acctttgtcc aagtccccta tttcccggac cttctaagcc cttttgggtg ctggtggtgg     960
ttgggggagt cctggcttgc tatagcttgc tagtaacagt ggcctttatt attttctggg    1020
tgaggagtaa gaggagcagg ctcctgcaca gtgactacat gaacatgact ccccgccgcc    1080
ccgggcccac ccgcaagcat taccagccct atgccccacc acgcgacttc gcagcctatc    1140
gctccagagt gaagttcagc aggagcgcag acgccccgc gtaccagcag gccagaacc     1200 agctctataa cgagctcaat ctaggacgaa gagaggagta cgatgttttg gacaagagac    1260
```
gtggccggga cccctgagatg gggggaaagc cgagaaggaa gaaccctcag gaaggcctgt    1320
acaatgaact gcagaaagat aagatggcgg aggcctacag tgagattggg atgaaaggcg    1380
agcgccggag gggcaagggg cacgatggcc tttaccaggg tctcagtaca gccaccaagg    1440
acacctacga cgcccttcac atgcaggccc tgccccctcg cactagt                  1487

<210> SEQ ID NO 2
<211> LENGTH: 21
<212> TYPE: DNA
<213> ORGANISM: Artificial sequence
<220> FEATURE:
<223> OTHER INFORMATION: TLR1/2 overlapA

<400> SEQUENCE: 2
gcggccgcaa ttgaagttat g                                              21

<210> SEQ ID NO 3
<211> LENGTH: 38
<212> TYPE: DNA
<213> ORGANISM: Artificial sequence
<220> FEATURE:
<223> OTHER INFORMATION: TLR1 overlap B1

<400> SEQUENCE: 3
catgcaggcc ctgccccctc gcaacatacc cttagaag                            38

<210> SEQ ID NO 4
<211> LENGTH: 38
<212> TYPE: DNA
<213> ORGANISM: Artificial sequence
<220> FEATURE:
<223> OTHER INFORMATION: TLR1 overlap B2

<400> SEQUENCE: 4
cttctaaggg tatgttgcga ggggcaggg cctgcatg                             38

<210> SEQ ID NO 5
<211> LENGTH: 28
<212> TYPE: DNA
<213> ORGANISM: Artificial sequence
<220> FEATURE:
<223> OTHER INFORMATION: TLR1 overlap C

<400> SEQUENCE: 5
actagttttc tttgcttgct ctgtcagc                                       28

<210> SEQ ID NO 6
<211> LENGTH: 42
<212> TYPE: DNA
<213> ORGANISM: Artificial sequence
<220> FEATURE:
<223> OTHER INFORMATION: TLR2 overlap B1

<400> SEQUENCE: 6
catgcaggcc ctgccccctc gccaggccaa aaggaagccc ag                       42

<210> SEQ ID NO 7
<211> LENGTH: 42
<212> TYPE: DNA
<213> ORGANISM: Artificial sequence
<220> FEATURE:
<223> OTHER INFORMATION: TLR2 overlap B2

<400> SEQUENCE: 7
ctgggcttcc ttttggcctg gcgagggggc agggcctgca tg                       42

```
<210> SEQ ID NO 8
<211> LENGTH: 27
<212> TYPE: DNA
<213> ORGANISM: Artificial sequence
<220> FEATURE:
<223> OTHER INFORMATION: TLR2 overlap C

<400> SEQUENCE: 8
actagtggac tttatcgcag ctctcag                                         27

<210> SEQ ID NO 9
<211> LENGTH: 1158
<212> TYPE: DNA
<213> ORGANISM: Artificial sequence
<220> FEATURE:
<223> OTHER INFORMATION: 28ZT1

<400> SEQUENCE: 9
gcggccgcaa ttgaagttat gtatcctcct ccttacctag acaatgagaa gagcaatgga      60
accattatcc atgtgaaagg gaaacacctt tgtccaagtc ccctatttcc cggaccttct     120
aagccctttt gggtgctggt ggtggttggg ggagtcctgg cttgctatag cttgctagta     180
acagtggcct ttattatttt ctgggtgagg agtaagagga gcaggctcct gcacagtgac     240
tacatgaaca tgactccccg ccgccccggg cccacccgca agcattacca gcccccatgcc    300 ccaccacgcg acttcgcagc ctatcgctcc agagtgaagt tcagcaggag cgcagacgcc     360
cccgcgtacc agcagggcca gaaccagctc tataacgagc tcaatctagg acgaagagag     420
gagtacgatg ttttggacaa gagacgtggc cgggaccctg agatgggggg aaagccgaga     480
aggaagaacc ctcaggaagg cctgtacaat gaactgcaga agataagat ggcggaggcc      540 tacagtgaga ttgggatgaa aggcgagcgc cggaggggca aggggcacga tggcctttac     600
cagggtctca gtacagccac caaggacacc tacgacgccc ttcacatgca ggccctgccc     660
cctcgcaaca tacccttaga agaactccaa agaaatctcc agtttcatgc atttatttca     720
tatagtgggc acgattcttt ctgggtgaag aatgaattat tgccaaacct agagaaagaa     780
ggtatgcaga tttgccttca tgagagaaac tttgttcctg gcaagagcat tgtggaaaat     840
atcatcacct gcattgagaa gagttacaag tccatctttg ttttgtctcc caactttgtc     900
cagagtgaat ggtgccatta tgaactctac tttgcccatc acaatctctt tcatgaagga     960
tctaatagct taatcctgat cttgctggaa cccattccgc agtactccat tcctagcagt    1020
tatcacaagc tcaaaagtct catggccagg aggacttatt ggaatggcc caaggaaaag     1080 agcaaacgtg ccttttttg gctaacttta agggcagcca ttaatattaa gctgacagag    1140
caagcaaaga aaactagt                                                 1158

<210> SEQ ID NO 10
<211> LENGTH: 1149
<212> TYPE: DNA
<213> ORGANISM: Artificial sequence
<220> FEATURE:
<223> OTHER INFORMATION: 28ZT2

<400> SEQUENCE: 10
gcggccgcaa ttgaagttat gtatcctcct ccttacctag acaatgagaa gagcaatgga      60
accattatcc atgtgaaagg gaaacacctt tgtccaagtc ccctatttcc cggaccttct     120
aagccctttt gggtgctggt ggtggttggg ggagtcctgg cttgctatag cttgctagta     180
```

| | |
|---|---|
| acagtggcct ttattatttt ctgggtgagg agtaagagga gcaggctcct gcacagtgac | 240 |
| tacatgaaca tgactcccg ccgcccggg cccacccgca agcattacca gccctatgcc | 300 |
| ccaccacgcg acttcgcagc ctatcgctcc agagtgaagt tcagcaggag cgcagacgcc | 360 |
| cccgcgtacc agcagggcca gaaccagctc tataacgagc tcaatctagg acgaagagag | 420 |
| gagtacgatg ttttggacaa gagacgtggc cgggaccctg agatgggggg aaagccgaga | 480 |
| aggaagaacc ctcaggaagg cctgtacaat gaactgcaga agataagat ggcggaggcc | 540 |
| tacagtgaga ttgggatgaa aggcgagcgc cggaggggca aggggcacga tggcctttac | 600 |
| cagggtctca gtacagccac caaggacacc tacgacgccc ttcacatgca ggccctgccc | 660 |
| cctcgccagg ccaaaaggaa gcccaggaaa gctcccagca ggaacatctg ctatgatgca | 720 |
| tttgtttctt acagtgagcg ggatgcctac tgggtggaga accttatggt ccaggagctg | 780 |
| gagaacttca atcccccctt caagttgtgt cttcataagc gggacttcat tcctggcaag | 840 |
| tggatcattg acaatatcat tgactccatt gaaaagagcc acaaaactgt ctttgtgctt | 900 |
| tctgaaaact tgtgaagag tgagtggtgc aagtatgaac tggacttctc ccatttccgt | 960 |
| ctttttgatg agaacaatga tgctgccatt ctcattcttc tggagcccat tgagaaaaaa | 1020 |
| gccattcccc agcgcttctg caagctgcgg aagataatga acaccaagac ctacctggag | 1080 |
| tggcccatgg acgaggctca gcgggaagga ttttgggtaa atctgagagc tgcgataaag | 1140 |
| tccactagt | 1149 |

<210> SEQ ID NO 11
<211> LENGTH: 486
<212> TYPE: DNA
<213> ORGANISM: Artificial sequence
<220> FEATURE:
<223> OTHER INFORMATION: TLR1 TIR domain

<400> SEQUENCE: 11

| | |
|---|---|
| aacatacccct tagaagaact ccaaagaaat ctccagtttc atgcatttat ttcatatagt | 60 |
| gggcacgatt ctttctgggt gaagaatgaa ttattgccaa acctagagaa agaaggtatg | 120 |
| cagatttgcc ttcatgagag aaactttgtt cctggcaaga gcattgtgga aaatatcatc | 180 |
| acctgcattg agaagagtta caagtccatc tttgttttgt ctcccaactt tgtccagagt | 240 |
| gaatggtgcc attatgaact ctactttgcc catcacaatc tctttcatga aggatctaat | 300 |
| agcttaatcc tgatcttgct ggaacccatt ccgcagtact ccattcctag cagttatcac | 360 |
| aagctcaaaa gtctcatggc caggaggact tatttggaat ggcccaagga aaagagcaaa | 420 |
| cgtggccttt tttgggctaa cttaagggca gccattaata ttaagctgac agagcaagca | 480 |
| aagaaa | 486 |

<210> SEQ ID NO 12
<211> LENGTH: 477
<212> TYPE: DNA
<213> ORGANISM: Artificial sequence
<220> FEATURE:
<223> OTHER INFORMATION: TLR2 TIR domain

<400> SEQUENCE: 12

| | |
|---|---|
| caggccaaaa ggaagcccag gaaagctccc agcaggaaca tctgctatga tgcatttgtt | 60 |
| tcttacagtg agcgggatgc ctactgggtg gagaacctta tggtccagga gctggagaac | 120 |
| ttcaatcccc ccttcaagtt gtgtcttcat aagcgggact tcattcctgg caagtggatc | 180 |
| attgacaata tcattgactc cattgaaaag agccacaaaa ctgtctttgt gctttctgaa | 240 |

```
aactttgtga agagtgagtg gtgcaagtat gaactggact tctcccattt ccgtctttt       300 gatgagaaca atgatgctgc cattctcatt cttctggagc ccattgagaa aaaagccatt      360
ccccagcgct tctgcaagct gcggaagata atgaacacca agacctacct ggagtggccc      420
atggacgagg ctcagcggga aggattttgg gtaaatctga gagctgcgat aaagtcc         477
```

<210> SEQ ID NO 13
<211> LENGTH: 162
<212> TYPE: PRT
<213> ORGANISM: Artificial sequence
<220> FEATURE:
<223> OTHER INFORMATION: TIR1 amino acid sequence

<400> SEQUENCE: 13

```
Asn Ile Pro Leu Glu Glu Leu Gln Arg Asn Leu Gln Phe His Ala Phe
1               5                   10                  15

Ile Ser Tyr Ser Gly His Asp Ser Phe Trp Val Lys Asn Glu Leu Leu
            20                  25                  30

Pro Asn Leu Glu Lys Glu Gly Met Gln Ile Cys Leu His Glu Arg Asn
        35                  40                  45

Phe Val Pro Gly Lys Ser Ile Val Glu Asn Ile Ile Thr Cys Ile Glu
    50                  55                  60

Lys Ser Tyr Lys Ser Ile Phe Val Leu Ser Pro Asn Phe Val Gln Ser
65                  70                  75                  80

Glu Trp Cys His Tyr Glu Leu Tyr Phe Ala His His Asn Leu Phe His
                85                  90                  95

Glu Gly Ser Asn Ser Leu Ile Leu Ile Leu Leu Glu Pro Ile Pro Gln
            100                 105                 110

Tyr Ser Ile Pro Ser Ser Tyr His Lys Leu Lys Ser Leu Met Ala Arg
        115                 120                 125

Arg Thr Tyr Leu Glu Trp Pro Lys Glu Lys Ser Lys Arg Gly Leu Phe
    130                 135                 140

Trp Ala Asn Leu Arg Ala Ala Ile Asn Ile Lys Leu Thr Glu Gln Ala
145                 150                 155                 160

Lys Lys
```

<210> SEQ ID NO 14
<211> LENGTH: 159
<212> TYPE: PRT
<213> ORGANISM: Artificial sequence
<220> FEATURE:
<223> OTHER INFORMATION: TIR2 amino acid sequence

<400> SEQUENCE: 14

```
Gln Ala Lys Arg Lys Pro Arg Lys Ala Pro Ser Arg Asn Ile Cys Tyr
1               5                   10                  15

Asp Ala Phe Val Ser Tyr Ser Glu Arg Asp Ala Tyr Trp Val Glu Asn
            20                  25                  30

Leu Met Val Gln Glu Leu Glu Asn Phe Asn Pro Pro Phe Lys Leu Cys
        35                  40                  45

Leu His Lys Arg Asp Phe Ile Pro Gly Lys Trp Ile Ile Asp Asn Ile
    50                  55                  60

Ile Asp Ser Ile Glu Lys Ser His Lys Thr Val Phe Val Leu Ser Glu
65                  70                  75                  80

Asn Phe Val Lys Ser Glu Trp Cys Lys Tyr Glu Leu Asp Phe Ser His
                85                  90                  95
```

```
Phe Arg Leu Phe Asp Glu Asn Asn Asp Ala Ala Ile Leu Ile Leu Leu
                100                 105                 110

Glu Pro Ile Glu Lys Lys Ala Ile Pro Gln Arg Phe Cys Lys Leu Arg
            115                 120                 125

Lys Ile Met Asn Thr Lys Thr Tyr Leu Glu Trp Pro Met Asp Glu Ala
        130                 135                 140

Gln Arg Glu Gly Phe Trp Val Asn Leu Arg Ala Ala Ile Lys Ser
145                 150                 155

<210> SEQ ID NO 15
<211> LENGTH: 803
<212> TYPE: DNA
<213> ORGANISM: Artificial sequence
<220> FEATURE:
<223> OTHER INFORMATION: CAR19 ScFv sequence

<400> SEQUENCE: 15
atgcttctcc tggtgacaag ccttctgctc tgtgagttac cacacccagc attcctcctg      60
atcccagaca tccagatgac acagactaca tcctccctgt ctgcctctct gggagacaga     120
gtcaccatca gttgcagggc aagtcaggac attagtaaat atttaaattg gtatcagcag     180
aaaccagatg gaactgttaa actcctgatc taccatacat caagattaca ctcaggagtc     240
ccatcaaggt tcagtggcag tgggtctgga acagattatt ctctcaccat tagcaacctg     300
gagcaagaag atattgccac ttactttgc aacagggta atacgcttcc gtacacgttc      360
ggagggggga ctaagttgga ataacaggc tccacctctg gatccggcaa gcccggatct      420 ggcgaggat ccaccaaggg cgaggtgaaa ctgcaggagt caggacctgg cctggtggcg      480
ccctcacaga gcctgtccgt cacatgcact gtctcagggg tctcattacc cgactatggt     540
gtaagctgga ttcgccagcc tccacgaaag ggtctggagt ggctgggagt aatatggggt     600
agtgaaacca catactataa ttcagctctc aaatccagac tgaccatcat caaggacaac     660
tccaagagcc aagttttctt aaaaatgaac agtctgcaaa ctgatgacac agccatttac     720
tactgtgcca acattatta ctacggtggt agctatgcta tggactactg gggtcaagga      780
acctcagtca ccgtctcctc agc                                              803

<210> SEQ ID NO 16
<211> LENGTH: 852
<212> TYPE: DNA
<213> ORGANISM: Artificial sequence
<220> FEATURE:
<223> OTHER INFORMATION: CAR22 ScFv sequence

<400> SEQUENCE: 16
atggttctgc tggtcacatc actgctcctc tgtgaactgc tcatcctgc ctttctgctc       60 attcccgaca ctgaagtcca gctcgtggaa tctggagggg gcctggtgaa acctggggga    120
tctctcaaac tgtcttgtgc cgcttctggc tttgcttta gcatctacga catgtcctgg     180
gtccggcaga cacctgaaaa acgcctggag tgggtcgcct acatttctag tggggcgga    240 acatactacc ccgataccgt gaagggacgc tttacaattt ctagggataa cgccaaaaac    300
accctgtacc tccagatgtc atccctgaaa tctgaggata ctgccatgta ctactgtgct    360
aggcattctg gctacggaac acattgggga gtgctcttcg cttactgggg ccaggggact    420
ctcgtcactg tctctgctgg cggggaggc tctggcggag cggatccgg aggcggaggg      480 agtgatattc agatgactca gaccacctct ctctgtccg cttctctggg cgatagagtg      540
acaatctcct gtcgggcatc acaggatatt agcaattacc tgaactggta ccagcagaaa    600
```

```
cccgatggaa ccgtcaaact gctcatctac tacacctcca tcctccactc tggcgtgcca    660
tctcgatttt ctggatctgg ctctggaacc gactactctc tcacaatctc caacctggaa    720
caggaggatt ttgccaccta cttttgtcag cagggcaata tctgccttg gacctttggg     780 ggcggaacca aactggaaat caaggccaaa acaaccccac cttccgtgta cggccgagtg    840 aaagaccta ag                                                         852

<210> SEQ ID NO 17
<211> LENGTH: 867
<212> TYPE: DNA
<213> ORGANISM: Artificial sequence
<220> FEATURE:
<223> OTHER INFORMATION: CARMeso ScFv sequence

<400> SEQUENCE: 17
atgcttctcc tggtgacaag ccttctgctc tgtgagttac cacacccagc attcctcctg    60
atcccaagcc aggtacagct gcagcagtca ggtccaggac tcgtgacgcc ctcgcagacc    120
ctctcactca cctgtgccat ctccggggac agtgtctcta gcaacagtgc tacttggaac    180
tggatcaggc agtccccatc gagaggcctt gagtggctgg aaggacata ctacaggtcc     240 aagtggtata cgactatgc agtatctgtg aaaagtcgaa tgagcatcaa cccagacaca     300
tccaagaacc agttctccct gcagctgaac tctgtgactc ccgaggacac ggctgtgtat    360
tactgtgcaa gaggaatgat gacttactat tacggtatgg acgtctgggg ccaagggacc    420
acggtcaccg tctcctcagg aattctagga tccggtggcg gtggcagcgg cggtggtggt    480
tccggaggcg gcggttctca gctgtgctg actcagtcgt cttccctctc tgcatctcct    540
ggagcatcag ccagtctcac ctgcaccttg cgcagtggca tcaatgttgg tccctacagg    600
atatactggt accagcagaa gccagggagt cctccccagt atctcctgaa ctacaaatca    660
gactcagata gcagcaggg ctctggagtc cccagccgct tctctggatc caaagatgct    720
tcggccaatg caggggtttt actcatctct gggctccggt ctgaggatga ggctgactat    780
tactgtatga tttggcacag cagcgctgct gtgttcggag gaggcaccca actgaccgtc    840
ctctccggaa ttctagaaca acagggt                                        867
```

CHIMERIC ANTIGEN RECEPTOR CONTAINING A TOLL-LIKE RECEPTOR INTRACELLULAR DOMAIN

CROSS-REFERENCE TO RELATED APPLICATIONS

This application is a 35 U.S.C. § 371 national stage filing of International Application No. PCT/CN2015/086352, filed Aug. 7, 2015. The entire contents of the aforementioned application are incorporated herein by reference.

TECHNICAL FIELD

The present invention relates to the technical field of cellular immunotherapy of tumors, and in particular, relates to chimeric antigen receptors, nucleic acids encoding the same and a cell expressing the same, and their uses in treating cancers associated with expression of specific antigens targeted by chimeric receptors.

BACKGROUND ART

Chimeric antigen receptor (CAR)-engineered T cells are those T cells expressing chimeric receptors, which can recognize specific antigens and can transmit signals, expressed on the surface thereof [1]. CAR T cells play an important role in treating cancer by expressing CAR molecules, which typically include an extracellular domain, a transmembrane region and an intracellular domain: the extracellular domain is a single-chain variable fragment (ScFv) formed by a heavy chain and a light chain variable regions of an antibody that connected each other via a peptide fragment; the intracellular domain is comprised of a variety of signaling molecules, including CD3zeta, CD28, OX-40, 4-1BB etc.; and the transmembrane region is originated from the transmembrane region of other molecules (such as CD8, CD4, CD28 and CD3zeta). The single chain variable fragment gene is isolated from hybridomas capable of generating monoclonal antibody which targeting specific antigen. T cells expressing CAR molecules directly recognize tumor cell-surface antigens independent of the expression of the major histocompatibility antigen type I on tumor cells. Thus T cells expressing CARs can be activated by tumor specific antigen and kill tumor cells effectively. In short, CAR T cells recognize specific molecules on the surface of tumor cells through antigen-antibody recognition manner, and then experience activation, proliferation and exert cytotoxic function through their intracellular signaling.

Currently, clinical researches on CAR T cells mainly focused on hematologic tumor, such as lymphoma, chronic lymphoid leukemia, acute lymphoid leukemia. However, some progress has been made in developing CAR T cells for treating other types of tumors, for example, anti-5T4 CAR T cells for treating solid tumors, anti-ROR-1 CAR T cells for treating solid tumors, anti-PCSA CAR T cells for treating solid tumors, anti-Mesothelin CAR T cells for treating pancreas mesothelioma, anti-EGFRvIII CAR T cells for treating glioma and glioblastoma, anti-CD22 CAR T cells for treating B-cell tumor, anti L1CAM CAR T cells for treating neuroblastoma, anti-MUC16 & IL6 CAR T cells for treating ovarian cancer, etc. In summary, the immunotherapy of chimeric antigen receptor T cells has been proved to effectively treat a variety of tumors, including leukemia resistant to chemotherapy and relapsed leukemia. But there are many problems in chimeric antigen receptor T cell therapy, such as cytolytic activity, persistance of CAR T cell and the formation of memory CAR T cells in vivo/patients.

The structure of CAR molecules has developed for multi generations. The structure of the first-generation CAR molecules comprises a single chain variable fragment (scFv) recognizing the specific surface antigen of tumor cells, a transmembrane domain and a intracellular domain of CD3ζ (TCR complex) for activating T cells. As the intracellular domain of the first generation of CAR only has CD3ζ signal transfer region without co-stimulatory signals, there is a big flaw in the function of the first generation of CAR T cells, which exhibit low levels in proliferation, persistence, effector functions and so on in a patient. In order to enhance the function of the first generation of CAR in activating T cell, the second generation of CAR has been developed, and an intracellular molecular signaling domain originated from costimulatory molecules (e.g., CD28, CD134 (OX-40), CD137 (4-1BB), etc.) has been introduced to the intracellular domain of the second generation of CAR. Clinical trials show that the second generation of CAR T cells show good proliferation, persistence and effector functions in a patient. Most of the clinical trials of the second generation of CAR T cells are the treatment for B-cell leukemia with anti-CD19 CAR T cells. CAR T cells have achieved success for leukemia in clinical trials, but lack efficacy in solid tumors. In order to further improve the efficacy of the CAR T cell therapy, the third generation CARs have been developed. Two costimulatory molecule signal transfer regions were introduced into the intracellular domain of the third generation CARs. Typically, one costimulatory signal is the CD28 intracellular domain and the other is the intracellular signal transfer region of CD134, CD137 or ICOS, etc. Different combinations of the costimulatory signals may affect the function and efficacy of the CAR T cells, and studies have shown that not all of the third-generation CARs are better than the second generation CARs. It can be seen that the structural design of CARs in the prior art is not very mature, and there still exists a need for further improving CAR molecules in T cell expansion, T cell function of killing tumor cells, T cell invasion and migration, eliminating immunosuppressive effect of regulatory T cells and promoting the formation of memory T cells, etc.

Janeway, an American immunologist, proposed pattern recognition theory, in which the natural immune response against the main target molecules signal is called pathogen-associated molecular pattern (PAMP); the corresponding recognition receptor is called pattern recognition receptor (PRR). Toll-like receptors (TLR) are PRR which can specifically recognize molecules derived from different microorganisms with conserved structures, and activate intrinsic immune responses. Toll-like receptors are a class of important receptors involved in innate immunity, and also a bridge connecting adaptive immunity and innate immunity. Ten types of TLR have been found in human, and are called TLR1-10 respectively. Most of TLRs work alone, except that TLR2 can form dimers with TLR1 or TLR6 respectively to identify microbial exogenous molecules and host endogenous molecules. Increasing studies show that TLR signaling plays an important role in tumor development and treatment. Because some TLRs are widely expressed on the cell surface of immune cells, and different TLR plays different roles in these cells. The researchers find that TCR-activated human T cells express TLR2 but not TLR4, and TLR2 provides co-stimulatory signal for activating T-cell function and maintaining memory T cells [2]. The effects of TLR2 on CD8-positive T cells include: down-regulating TCR signal strength threshold required for activating T cells, prompting the formation of memory T cells under low TCR signal [7]. TLR1/TLR2 agonists can effectively eliminate the function of regulatory T cells by down-regulating the expression of Foxp3 [3, 4, 5]. Further studies show that, TLR1/TLR2 agonists can induce tumor regression by reducing the regulatory T cells and up-regulating the function of cytotoxic T cells [6].

REFERENCES

1. Restifo, N. P., Dudley, M. E., and Rosenberg, S. A. (2012). Adoptive immunotherapy for cancer: harnessing the T cell response. Nature reviews Immunology 12, 269-281.
2. Komai-Koma, M., L. Jones, G. S. Ogg, D. Xu, and F. Y. Liew. 2004. TLR2 is expressed on activated T cells as a costimulatory receptor. Proc. Natl. Acad. Sci. USA 101: 3029-3034.
3. Takeuchi, O., S. Sato, T. Horiuchi, K. Hoshino, K. Takeda, Z. Dong, R. L. Modlin, and S. Akira. 2002. Cutting edge: role of Toll-like receptor 1 in mediating immune response to microbial lipoproteins. J. Immunol. 169: 10-14.
4. Liu, H., M. Komai-Koma, D. Xu, and F. Y. Liew. 2006. Toll-like receptor 2 signaling modulates the functions of CD4+ CD25+ regulatory T cells. Proc. Natl. Acad. Sci. USA 103: 7048-7053.
5. Sutmuller, R. P., M. H. den Brok, M. Kramer, E. J. Bennink, L. W. Toonen, B. J. Kullberg, L. A. Joosten, S. Akira, M. G. Netea, and G. J. Adema. 2006. Toll-like receptor 2 controls expansion and function of regulatory T cells. J. Clin. Invest. 116: 485-494.
6. Zhang, Y., Luo, F, Cai, Y., Liu, N., Wang, L., Xu, D., and Chu, Y. 2011. TLR1/TLR2 agonist induces tumor regression by reciprocal modulation of effector and regulatory T cells. Journal of immunology 186, 1963-1969.
7. Mercier, B. C., Cottalorda, A., Coupet, C. A., Marvel, J., and Bonnefoy-Berard, N. (2009). TLR2 engagement on CD8 T cells enables generation of functional memory cells in response to a suboptimal TCR signal. Journal of immunology 182, 1860-1867.

CONTENTS OF THE INVENTION

Object of the present invention is to provide a new third generation of chimeric antigen receptor (CAR), a nucleic acid encoding the same and a cell expressing the same, and their use in treating cancers. Compared to the prior art, the chimeric antigen receptor of the present invention has significant advantages in activating T cell activity, eliminating immunosuppressive action of regulatory T cells and forming memory T cells.

The present invention achieves the above object by the following technical solutions:

In the first aspect, the present invention provides a chimeric antigen receptor, comprising an extracellular domain capable of binding to an antigen, a transmembrane domain and at least one intracellular domain. Wherein, "intracellular domain" refers to any oligopeptide or polypeptide known to act as transmission signal in a cell to make the domain for activation or inhibition of the biological processes function. And said at least one intracellular domain refers to Toll-like receptor 1 and/or Toll-like receptor 2 intracellular domains, or intracellular domains formed by Toll-like receptor 1 and/or Toll-like receptor 2 intracellular domains connecting in series with other signal transfer regions such as CD3ζ, CD28, 41BB and the like.

The Toll-like receptor (called TLR) 1 or Toll-like receptor 2 intracellular domain is intracellular signaling region, also known as TIR domain. Toll-like receptors is a type I transmembrane receptors for recognizing microorganisms invading the body and thus activating responses of the immune cells. Toll-like receptors play a key role in the innate immune system. Toll-like receptors are one class of pattern recognition receptors (PRR) and recognizes pathogen molecules different from host. Toll-like Receptor 1 and Toll-like receptor 2 are important members of the Toll-like receptor family.

With respect to the above CAR molecules, preferably, the antigen can be a tumor associated antigen, and the tumor associated antigen includes 5T4, α5β1-integrin, 707-AP, AFP, ART-4, B7H4, BAGE, β-catenin/m, Bcr-abl, MN/C IX antibody, CA125, CAMEL, CAP-1, CASP-8, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HST-2, hTERT (or hTRT), iCE, IGF-1R, IL-2R, IL-5, KIAA0205, LAGE, LDLR/FUT, MAGE, MART-1/melan-A, MART-2/Ski, MC1R, Mesothelin, myosin/m, MUC1, MUM-1, MUM-2, MUM-3, NA88-A, PAP, protease-3, p190minor bcr-abl, Pml/RARα, PRAME, PSA, PSM, PSMA, RAGE, RU1 or RU2, SAGE, SART-1 or SART-3, survivin, TEL/AML1, TGFβ, TPI/m, TRP-1, TRP-2, TRP-2/INT2, VEGF, WT1, NY-Eso-1 or NY-Eso-B, and so on; more preferably, the tumor associated antigen is CD19 or Mesothelin. The antigens mentioned by the present invention may also be inflammatory cell surface molecules present in autoimmune diseases or TCR causing autoimmune responses.

Preferably, said extracellular domain capable of binding to an antigen refers to a single chain variable fragment of an antibody binding to a target antigen.

In a particular embodiment, the above CAR molecules can only contain Toll-like receptor 1 and/or Toll-like receptor 2 intracellular domain as its intracellular domain, and can also contain another one or more (for example two or three) intracellular domains in addition to Toll-like receptor 1 and/or Toll-like receptor 2 intracellular domain.

For example, in a preferred embodiment, in addition to Toll-like receptor 1 and/or Toll-like receptor 2 intracellular domains, the intracellular domain further includes CD3ζ intracellular domain; more preferably, the Toll-like receptor 1 and/or Toll-like receptor 2 intracellular domain are arranged on the C-terminal side of the CD3ζ intracellular domain.

In a further preferred embodiment, in addition to Toll-like receptor 1 and/or Toll-like receptor 2 intracellular domain, and CD3ζ intracellular domain, the intracellular domain further includes CD28 intracellular domain.

In one particular embodiment, the intracellular domain comprises CD28 intracellular domain, CD3ζ intracellular domain and Toll-like receptor 1 and/or Toll-like receptor 2 intracellular domain connected with each other in sequence from the N-terminal side.

In addition, the chimeric antigen receptor in which the intracellular domain comprises two or more intracellular domains connected in series with each other is also encompassed in the present invention; and alternatively, the Toll-like receptor 1 and/or Toll-like receptor 2 intracellular domains may be arranged on the N-terminal side of CD3ζ or CD28 within the chimeric antigen receptor intracellular domains.

In a preferred embodiment, the chimeric antigen receptor includes, in sequence from the N-terminal side, a single chain variable region of an antibody against tumor associated antigen as the extracellular domain, a transmembrane domain and an intracellular domain of CD28, CD3ζ intracellular domain, Toll-like receptor 1 and/or Toll-like receptor 2 intracellular domain.

In the second aspect, the present invention provides a nucleic acid encoding the chimeric antigen receptor according to the first aspect.

In the third aspect, the present invention provides a chimeric antigen receptor expressing cell, into which the nucleic acid according to the second aspect is introduced; preferably, the cell is a T cell or a cell population containing T cells.

In the fourth aspect, the present invention provides a method for preparing the chimeric antigen receptor expressing cell according to the third aspect, comprising the step of introducing the nucleic acid according to the second aspect into the cell; preferably, the cell is T cell or a cell population containing T cells.

In the fifth aspect, the present invention provides the use of the chimeric antigen receptor according to the first aspect, the nucleic acid according to the second aspect, or the chimeric antigen receptor expressing cell according to the third aspect in manufacturing a medicament for treating tumor.

Preferably, the tumor is a solid tumor or a hematological tumor.

In a particular example of the use provided by the present invention, the chimeric antigen receptor according to the first aspect comprises a single chain variable region of an antibody against CD19 or Mesothelin antigen as the extracellular domain, and the tumor to be treated is hematological tumor or solid tumor, preferably is those associated with the expression of CD19 or Mesothelin, and more preferably, is B-ALL or lung cancer.

It is worth noting that the CARs of the present invention are characterized by that they contain Toll-like receptor 1 and/or Toll-like receptor 2 intracellular domains as their intracellular domain. The Toll-like receptor 1 and/or Toll-like receptor 2 intracellular domains include the variants thereof with the same function. The term "variant" refers to any variant with substitution, deletion or addition of one or a few to several amino acids, with the proviso that the variant has retained substantially the same function as the original sequence.

Advantageous Effects

The present invention promotes the proliferation and killing effect of the CAR T cells and the formation of memory CAR T cells, thereby increasing tumor immunological effect and therapeutic effect by introducing a Toll-like receptor 1 and/or Toll-like receptor 2 intracellular signaling domain into CAR molecules. Compared with the CAR molecules of the prior art, the CAR molecules of the invention have the following advantages: 1) promoting anti-apoptosis and proliferation of the CAR T cells in vitro and in vivo; 2) significantly increasing the antitumor function of the CAR T cells; 3) reducing the immunosuppressive action of the regulatory T cells; 4) conducive to the formation of memory CAR T cells and the inhibition of tumor recurrence; 5) promoting T cells migrating and invading into tumor tissue; in view of these advantages, CAR molecules of the present invention have good prospects for clinical application in tumor therapy.

EMBODIMENTS

Figure 1:
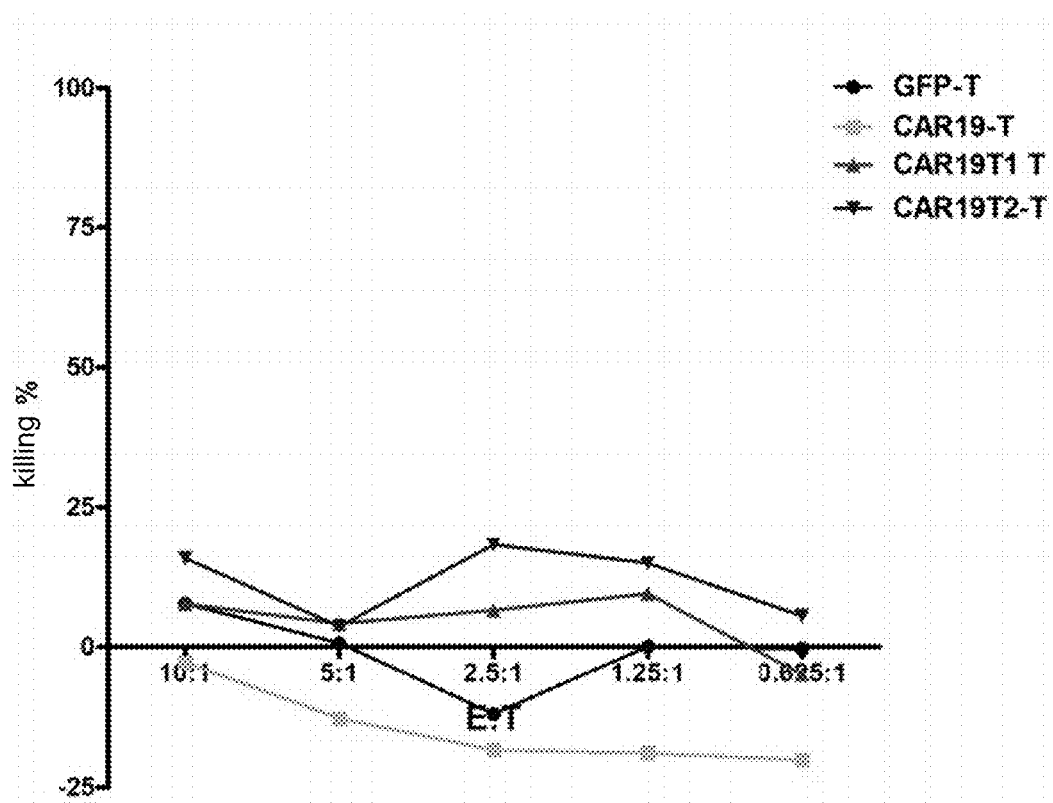
FIG. 1 shows the in vitro killing efficacy of GFP T, CAR19 T, CAR19T1 T and CAR19T2 T cells against K562-GL cells which do not express CD19.
Figure 2:
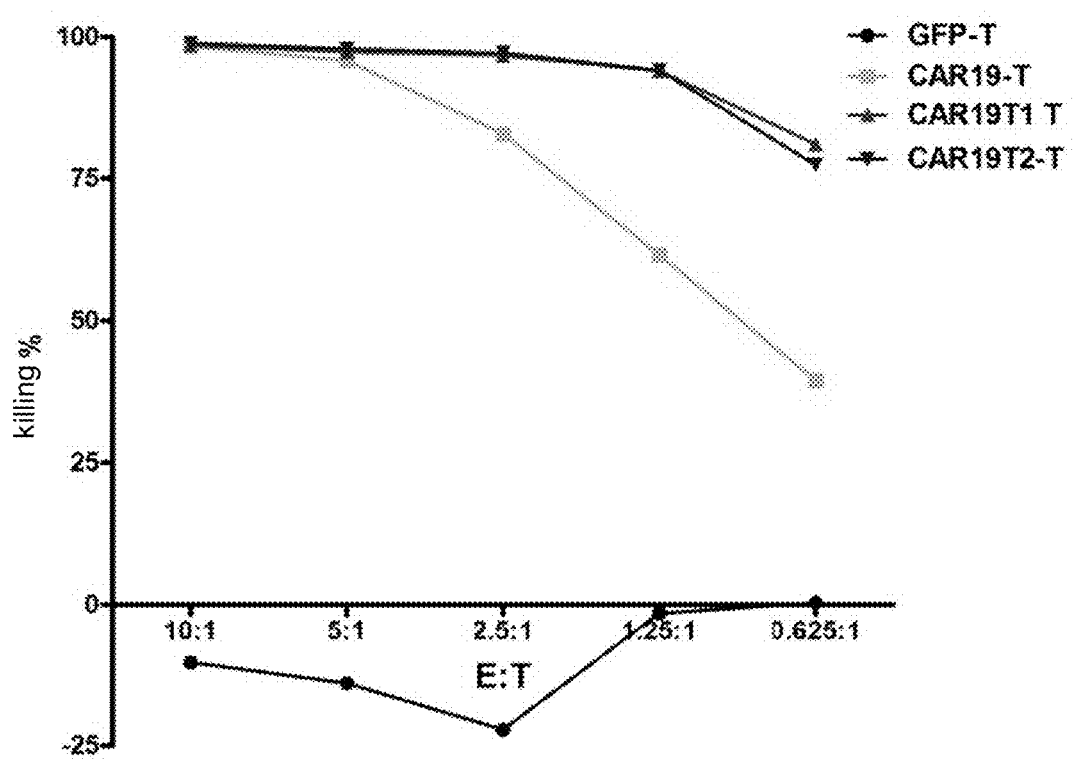
FIG. 2 shows the in vitro killing efficacy of GFP T, CAR19 T, CAR19T1 T and CAR19T2 T cells against K562-CD19-GL cells which express CD19.
Figure 3:
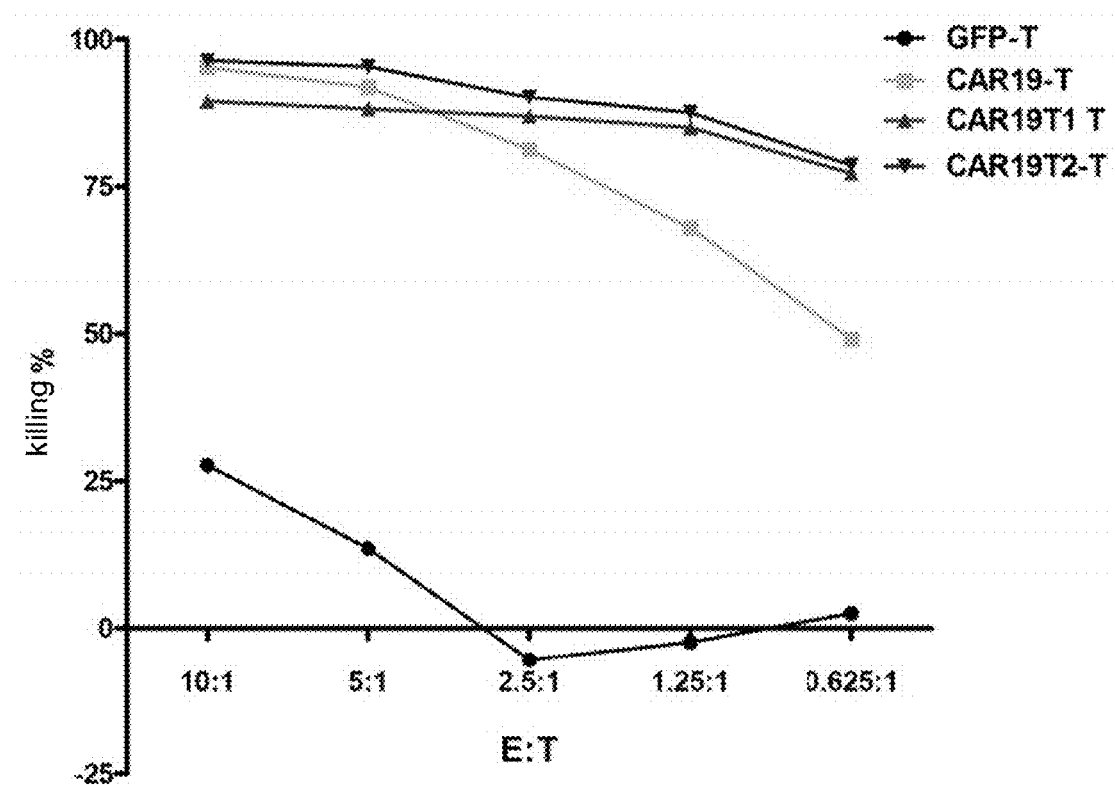
FIG. 3 shows the in vitro killing efficacy of GFP T, CAR19 T, CAR19T1 T and CAR19T2 T cells against NALM6-GL cells which express CD19.
Figure 4:
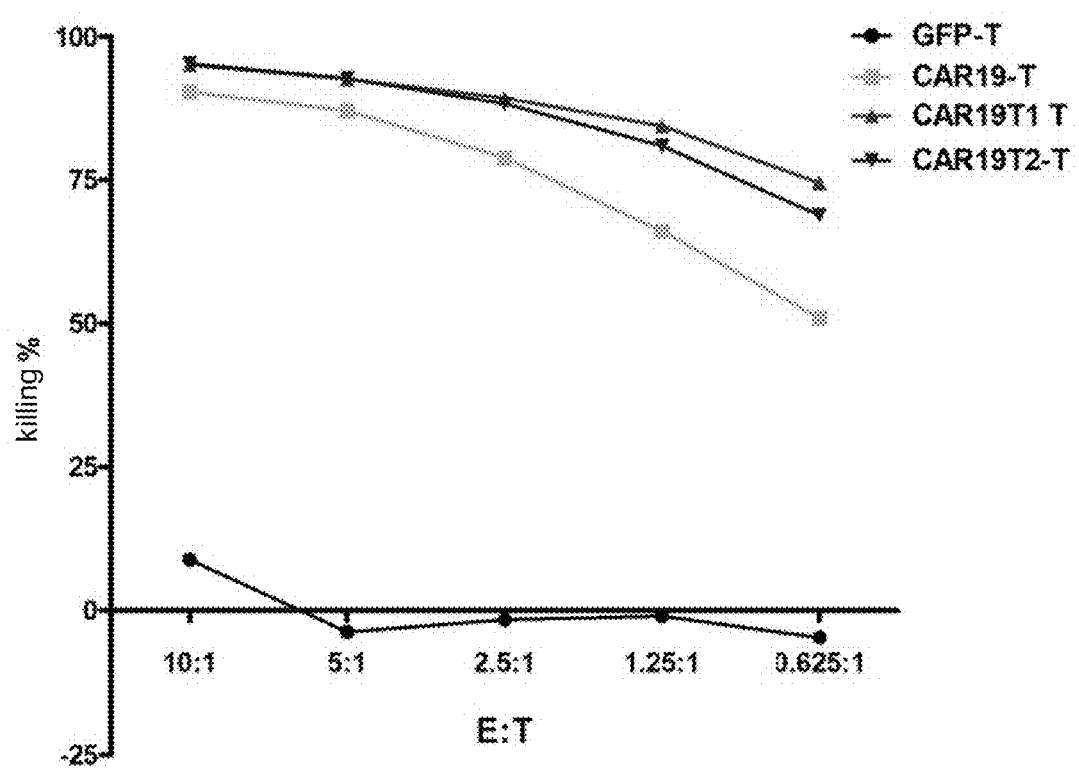
FIG. 4 shows the in vitro killing efficacy of GFP T, CAR19 T, CAR19T1 T and CAR19T2 T cells against REH-GL cells which express CD19.

To facilitate understanding of the present invention, the examples of the present invention are exemplified as follows. One skilled in the art should appreciate that the examples are offered to merely aid in understanding the invention and should not be regarded as particular limit to the present invention.

General Approach

In general, TLR1 and/or TLR2 signaling domain sequences are inserted into the intracellular domains of the anti-human CD19 chimeric antigen receptor for treating hematological tumor (B acute lymphoid leukemia, B-ALL) and anti-human Mesothelin chimeric antigen receptor for treating solid tumors (lung cancer) respectively to build the following four new chimeric antigen receptors: anti-CD19 ScFv-CD28-CD3ζ-TLR1/TLR2 and anti-Mesothelin ScFv-CD28-CD3ζ-TLR1/TLR2, hereinafter abbreviating the four chimeric antigen receptors as: CAR19T1, CAR19T2, CAR-MesoT1 and CARMesoT2 respectively. And the proliferation, anti-tumor function and the formation of memory of the CAR T cells expressing the above CAR molecules are assessed by in vivo and in vitro experiments.

Construction of CAR Plasmid

As described above, a CAR molecule comprises an extracellular region, a transmembrane domain, and an intracellular domain, and therefore, constructing steps of the CAR plasmid used by the following Examples comprises:

First, DNA encoding the respective gene required for CAR plasmid is obtained by gene synthesis, such DNA comprising: ScFv sequences of the anti-CD19 antibody, ScFv sequences of the anti-Mesothelin antibody, CD28 transmembrane and signaling sequence, TLR1 signaling sequence, TLR2 signaling sequence and CD3ζ signaling sequence;

Then, as required, the above synthesized gene sequences are connected in series with each other by steps of enzymatic digestion and connection, i.e., to obtain the novel CAR molecule of the invention. The sequence structures are as follows:

CAR19T1: anti-CD19 antibody ScFv (extracellular region), CD28 transmembrane and intracellular signaling region, CD3ζ signaling domain+TLR1 signaling domain;

CAR19T2: anti-CD19 antibody ScFv (extracellular region), CD28 transmembrane and intracellular signaling region, CD3ζ signaling domain, TLR2 signaling domain;

CAR19: anti-CD19 antibody ScFv (extracellular region), CD28 transmembrane and intracellular signaling region, CD3ζ signaling domain.

CARMesoT1: Anti-Mesothelin ScFv (extracellular region), CD28 transmembrane and intracellular signaling region, CD3ζ signaling domain, TLR1 signaling domain;

CARMesoT2: Anti-Mesothelin ScFv (extracellular region), CD28 transmembrane and intracellular signaling region, CD3ζ signaling domain, TLR2 signaling domain;

CARMeso: Anti-Mesothelin ScFv (extracellular region), CD28 transmembrane and intracellular signaling region, CD3ζ signaling domain;

Sequences of the above six kinds of CARs are inserted into the second generation of lentiviral vector pWPXLd-GFP to construct pWPXLd-CAR19T1-GFP, pWPXLd-CAR19T2-GFP, pWPXLd-CAR19-GFP, pWPXLd-CARMesoT1-GFP, pWPXLd-CARMesoT2-GFP and pWPXLd-CARMeso-GFP plasmid respectively.

SPECIFIC EXAMPLE

Example 1 Preparation of CAR19T1, CAR19T2 Plasmid

The plasmids carrying chimeric antigen receptor genes containing TLR1 and/or TLR2 intracellular domain of the present invention were prepared as follows:
(1) Plasmid pUC57-CAR19 containing CAR19 gene (SEQ ID NO.1) is obtained by gene synthesis; the CAR19 gene comprises an anti-CD19 mAb ScFv (SEQ ID NO.15), CD28 transmembrane region and intracellular region, CD3ζ intracellular region.
(2) The resultant plasmid pUC57-CAR19 was digested with endonuclease PmeI and SpeI, to obtain CAR19 gene, and then the CAR19 gene was connected into lentivirus vector pWPXLd-GFP to construct pWPXLd-CAR19-GFP.
(3) The resultant pWPXLd-CAR19-GFP plasmid was digested with endonuclease NotI and SpeI to obtain intracellular fragment 28Z of CAR19 gene.
(4) The cDNA of TLR1 and the fragment 28Z were used as templates to obtain 28ZT1 (SEQ ID NO. 9) by overlapping PCR with four primers (SEQ ID NO. 2-5); Similarly, the cDNA of TLR2 and the fragment 28Z were used as templates to obtain 28ZT2 (SEQ ID NO. 10) with four primers (SEQ ID NO. 2, 6, 7, 8).
(5) The 28zT1 and 28zT2 fragments digested with NotI and SpeI were then ligated with the ScFv of CAR19 in pUC57, generating pUC57-CAR19T1 and pUC57-CAR19T2 respectively.
(6) Finally, pWPXLd-CAR19T1-GFP or pWPXLd-CAR19T2-GFP plasmid was obtained respectively by digesting with endonuclease PmeI and SpeI, and replacing CAR19 in pWPXLD-CAR19-GFP with CAR19T1 or CAR19T2.

Intracellular signaling domains of TLR1 and TLR2 are called Toll/interleukin-1 receptor 1 (TIR1) (sequence shown in SEQ ID NO.11) and Toll/interleukin-1 receptor 2 (TIR2) (sequence shown in SEQ ID NO.12), respectively; TIR1 is the formed by 162 amino acids from the C-terminal of TLR1 (a.a. 625-786, sequence shown in SEQ ID NO.13), and TIR2 is formed by 159 amino acids from the C-terminal of TLR2 (a.a. 626-784, sequence shown in SEQ ID NO.14).

Example 2 Preparation of CARMesoT1, CARMesoT2 and CAR22 Plasmids

Mesothelin monoclonal antibody scFv domain sequence (SEQ ID NO.17) was obtained by gene synthesis, and pWPXLd-CARMesoT1-GFP or pWPXLd-CARMesoT2-GFP was obtained by digesting with endonuclease PmeI and NotI, and replacing CD19 monoclonal antibody scFv domains in pWPXLd-CAR19T1-GFP and pWPXLd-CAR19T2-GFP respectively with Mesothelin monoclonal antibody scFv domain.

In addition, CAR22, an anti-CD22 chimeric antigen receptor was used as negative control of CARMesoT1/T2. Plasmid containing CAR22 was pWPXLd-CAR22, of which the construction mainly through synthesizing anti-CD22 ScFv fragment (ie, SEQ ID NO.16), replacing anti-CD19 ScFv in CAR19 plasmid with the same by enzymatic digestion and ligation.

Example 3 Packaging of Lentiviral Vectors Expressing CARs

CAR plasmids of the present invention prepared in Example 1 and 2 and the related control plasmids were used, via lentiviral packaging, to obtain 8 kinds of recombinant lentiviruses expressing GFP (blank), CAR19T1-GFP, CAR19T2-GFP, CAR19-GFP, CARMesoT1-GFP, CARMesoT2-GFP, CARMeso-GFP, CAR22-GFP (negative control) respectively.

Specific steps were as follows:
293T cells were cultured in 150 mm dishes with the culture medium consisting of DMEM high glucose culture medium+10% FBS (fetal bovine serum)+1% penicillin/streptomycin penicillin/streptomycin;
When the density of 293T cells in 150 mm dishes reached 80-90%, the culture medium was changed with DMEM high glucose medium+1% FBS+1% penicillin/streptomycinpenicillin/streptomycin;
After replacing the culture medium and culturing for 2-6 hours, six kinds of pWPXLd-CARX-GFP plasmids (ie, including CAR19T1, CAR19T2, CAR19, CARMesoT1, CARMesoT2, CARMeso respectively) or blank control plasmid pWPXLd-GFP were co-transfected into 293T cells with plasmid pMD2.G and psPAX2 and the transfection reagent PEI, wherein the reagents and the doses thereof were as follows:

| reagent | dose |
| --- | --- |
| six kinds of pWPXLd-CARX-GFP plasmids or control plasmid pWPXLd-GFP | 9 μg |
| pMD2.G | 3 μg |
| psPAX2 | 12 μg |
| PEI | 72 μg |

The lentiviral supernatant was collected and fresh culture medium (DMEM high glucose medium+1% FBS+1% penicillin/streptomycin) was added at 24, 48 and 72 hours after transfection respectively;
After completing the collection of the supernatant of culture medium, the collected supernatant was centrifuged at 2500 g for 0.5 hours;

The centrifuged supernatant was filtrated with 0.45 um filter, and then centrifuged at 28000 rpm for 1.5 hours with ultra high-speed centrifuge;

After ultracentrifugation, the supernatant was removed gently, and 200 ul PBS was added to dissolve the precipitation under 4 degrees for 12-16 hours, and thereby to obtain six kinds of CAR lentiviruses or blank control GFP lentivirus;

After the viruses were dissolved, the virus solution was subpackaged in PCR tubes, and frozen at −80 □ for use.

Example 4 Transfection of Human T Cells with CAR Lentivirus

Isolation and purification of T cells: PBMCs from healthy donors were isolated by Ficoll density gradient method, and red blood cells were depleted with red blood cell lysis buffer, followed byMACS sorting of T cells through PanT isolation Kit.

The sorted T cells were resuspended with culture medium (AIM-V culture medium+5% FBS+penicillin 100 U/ml+streptomycin 0.1 mg/ml) to $2.5 \times 10^6$ cells/ml for use;

T cell stimulation by beads coated with anti-CD2, CD3, CD28 antibody (Origin of product: Miltenyi Biotech), ie. the beads were mixed with T cells at the ratio of 1:2, the final density of T cells was $5 \times 10^6$ cells/ml/cm$^2$; after a thorough mixing, T cells were cultured in a 37 □, 5% $CO_2$ incubator for 48 hours.

Lentiviral transfection of T cells: the beads are removed from the activated T cells and T cells were centrifuged at 300 g for 5 min, and resuspended with fresh medium, followed by addition of the lentiviruses (at MOI=10) expressing CARs or GFP, and then 8 μg/ml of polybrene and 300 IU/ml IL-2 were added. T cells were cultured in a 37 □, 5% $CO_2$ incubator for 24 hours, and centrifuged at 300 g for 5 min and resuspended with fresh medium containing 300 IU/ml IL-2.

Expansion of CAR T cells: the density of CAR T cells was maintained at $1-2 \times 10^6$ cells/ml, and half of the medium was replaced once every 2-3 days. Two weeks later, CAR T cells could be amplified up to 100 times. GFP-positive cells were successfully transfected cells, and the percentages of GFP-positive cells were detected by flow cytometry. (abbreviated as CAR19T1-GFP T, CAR19T2-GFP T, CAR19-GFP T, CARMesoTLR1-GFP T, CARMesoTLR2-GFP T, CARMeso-GFP T respectively) or blank control T cells (GFP T).

Example 5 Enhanced Antitumor Efficacy in vitro of CAR T Cells when TLR1 or TLR2 was Incorporated GFP T (blank), CAR19T1 T, CAR19T2T and CAR19 T (control), or GFP T, CARMesoT1 T, CARMesoT2 T and CARMeso T (control) cells prepared in Example 4 are mixed with $1 \times 10^4$ tumor cells respectively in different proportions and the resultant mixtures were added to 96-well U-shaped plate, with triple wells for each group, and a group containing tumor cells alone as a positive control. After centrifugation at 250 g for 5 min, cells were cultured in 37 degrees 5% $CO_2$ incubator for 18 h.

T0 compare the effector function of GFP T, CAR19 T, CAR19T1 T and CAR19T2 T cells against hematological tumor in vitro, NALM6-GL (GFP$^+$ Luciferase), REH-GL, K562-GL and K562-CD19-GL, four kinds of leukemia or lymphoma cell line expressing luciferase, were selected as tumor cells to be tested; when validating the recognition and killing function of GFP T, CARMeso T, CARMesoT1 T and CARMesoT2 T cells on solid tumor cells in vitro, mesothelin positve A549-GL human lung adenocarcinoma cell line expressing luciferase was selected as tumor cells to be tested.

Luciferase killing assay: 18 hours after co-culture of CAR T cells with tumor cells (tumor cells cultured alone were used as control group in the experiment), 100 μl/well of luciferase substrate (1×) was added to each well of the plate, and the cells were resuspended and mixed, immediately followed by measuring RLU (relative light unit) through a multifunctional microplate reader, measuring time being set to one second. Calculation formula of killing rate was as follows: 100%×(numerical readings for control wells−numerical readings for experimental wells)/numerical readings for control wells (readings of blank control without cells could be ignored); the results were shown in FIGS. 1-4.

The results showed that, compared with CAR19 T cells, the in vitro killing capacities of CAR19T1 and CAR19T2 T cells against target tumor cells expressing CD19 were significantly higher, especially when E: T (ie, the ratio of effector T cells to target cells) was very low (see FIGS. 1-4).

Figure 5:
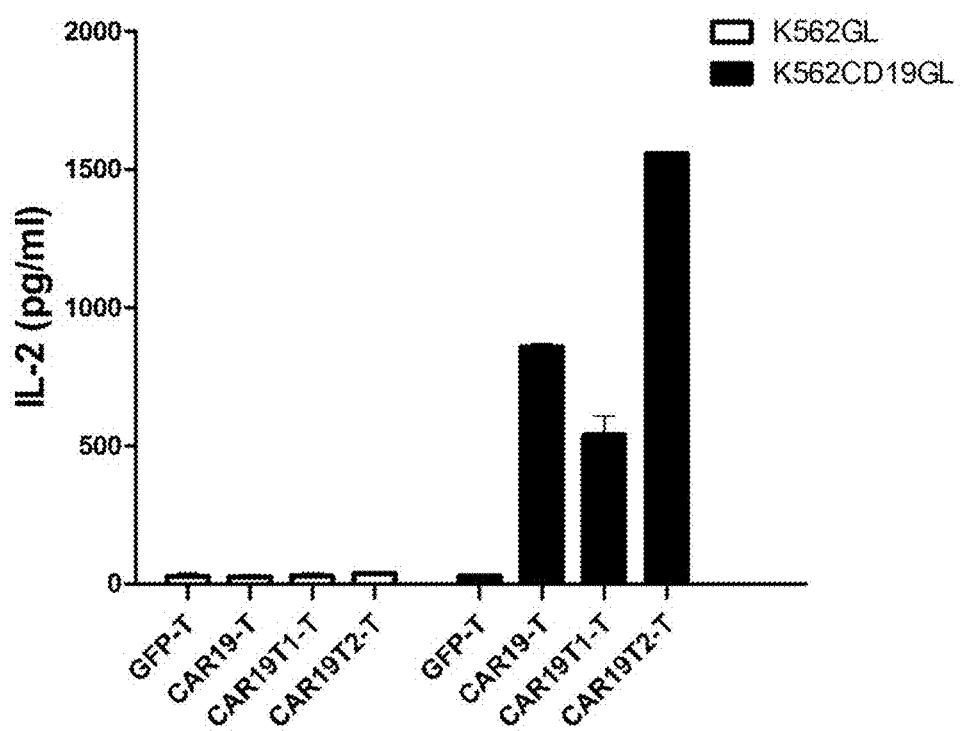
FIG. 5 shows the level of IL-2 in supernatant after coculture of GFP T, CAR19 T, CAR19T1 T and CAR19T2 T cells respectively with K562GL or K562-CD19-GL cells for 18 h.

After GFP T, CAR19 T, CAR19T1 T, CAR19T2 T cells were co-cultured with K562GL or K562-CD19-GL cells respectively for 18 h, the IL-2 levels in the supernatant were detected, and the results were shown in FIG. 5; FIG. 5 showed that the level of IL-2 secreted by CAR19T2 T cells was higher than that secreted by CAR19 T cells, indicating that the addition of intracellular domain of TLR2 improved the IL-2 secretion of CAR T cells.

Figure 6:
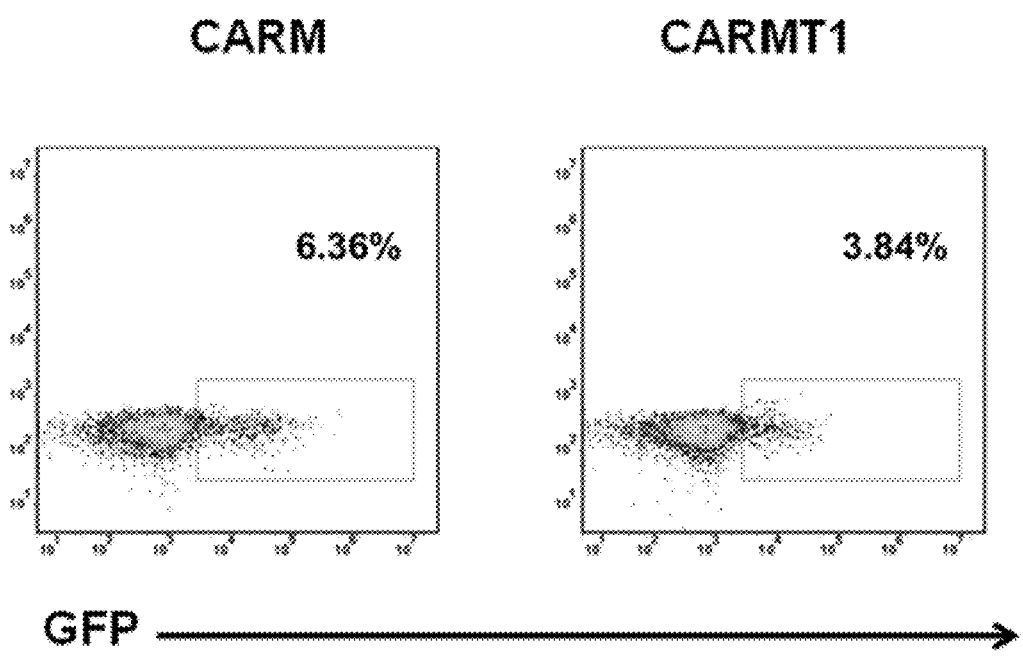
FIG. 6 shows the transduction efficiency of CARMeso and CARMesoT1 T cells
Figure 7:
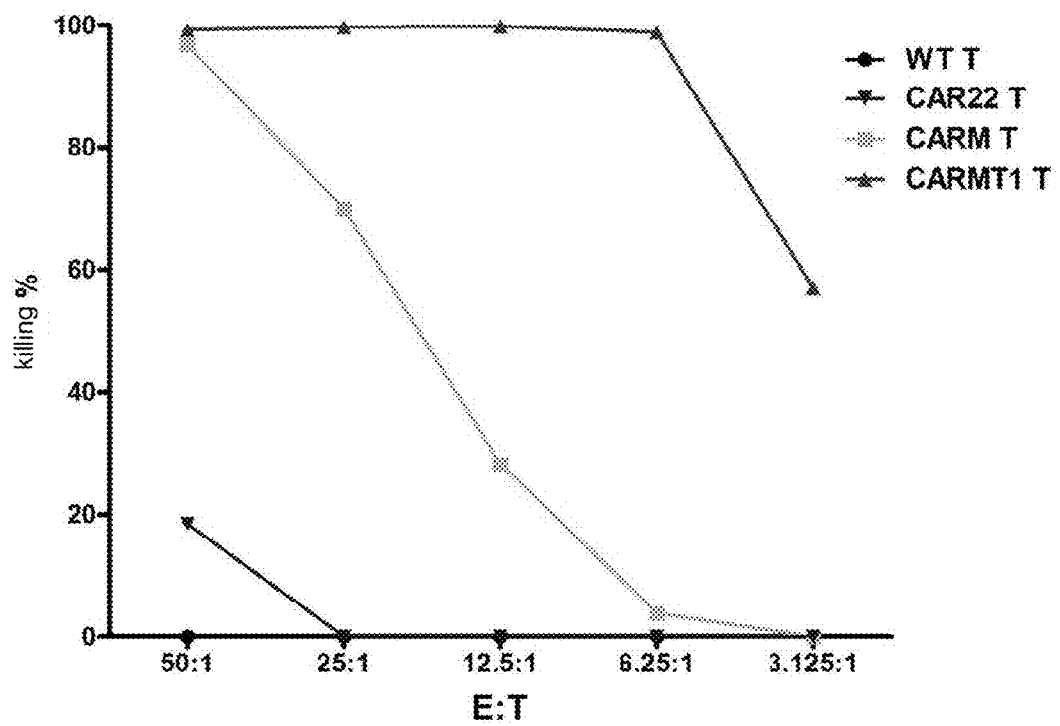
FIG. 7 shows the in vitro killing efficacy of the CAR T cells in FIG. 6 against A549GL cells; wild-type T cells, as well as CAR T cells against CD22 molecule are used as controls.

In addition, even when the percentages of CAR T cells were very low (as shown in FIG. 6), the in vitro killing capacity of CARMesoT1 T cells against target cells expressing Mesothelin was significantly higher than CARMeso T cells (see FIG. 7).

Figure 8:
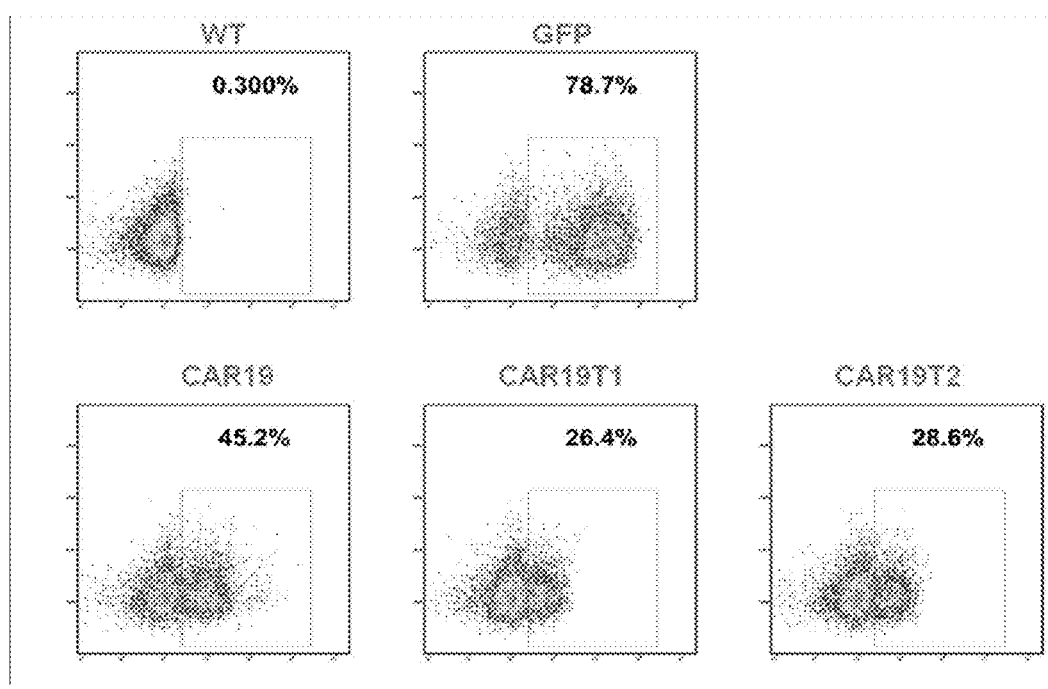
FIG. 8 shows the transduction efficiency of GFP, CAR19, CAR19T1 and CAR19T2 T cells.

Example 6 CAR19T1/T2 T Cells with Enhanced Anti-tumor Efficacy in vivo, Compared with CAR19 T Cells For the purpose of comparing the efficacy of GFP T, CAR19 T, CAR19T1 T and CAR19T2 T cells against solid tumors, identical number ($2 \times 10^5$) of NALM6 cells were subcutaneously transplanted into 16 of NSI (NOD/ SCIDIL2rg$^{-/-}$) immunodeficient mice; 2 days and 9 days after NALM6 cell transplantation, $2 \times 10^6$ T cells (four groups: GFP T, CAR19 T, CAR19T1 T, CAR19T2, four mice for each group, the proportion of positive cells as shown in FIG. 8) were intravenously injected into the NSI immunodeficient mice transplanted with NALM6 cells; on day 33, all the mice were euthanized for taking the tumors and weighed the same.

Figure 9:
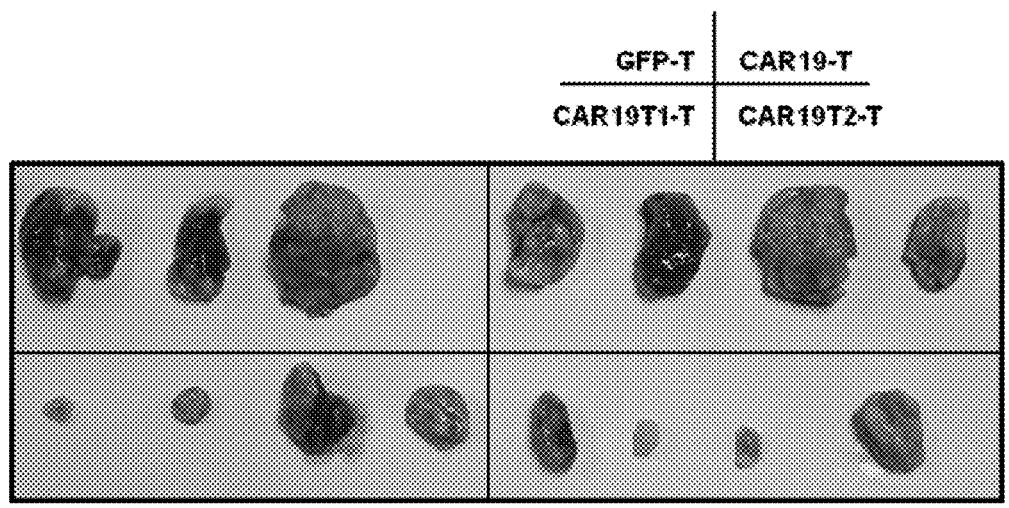
FIG. 9 shows the size of NALM6 tumors in immunodeficient mice treated with CAR T cells in FIG. 8.
Figure 10:
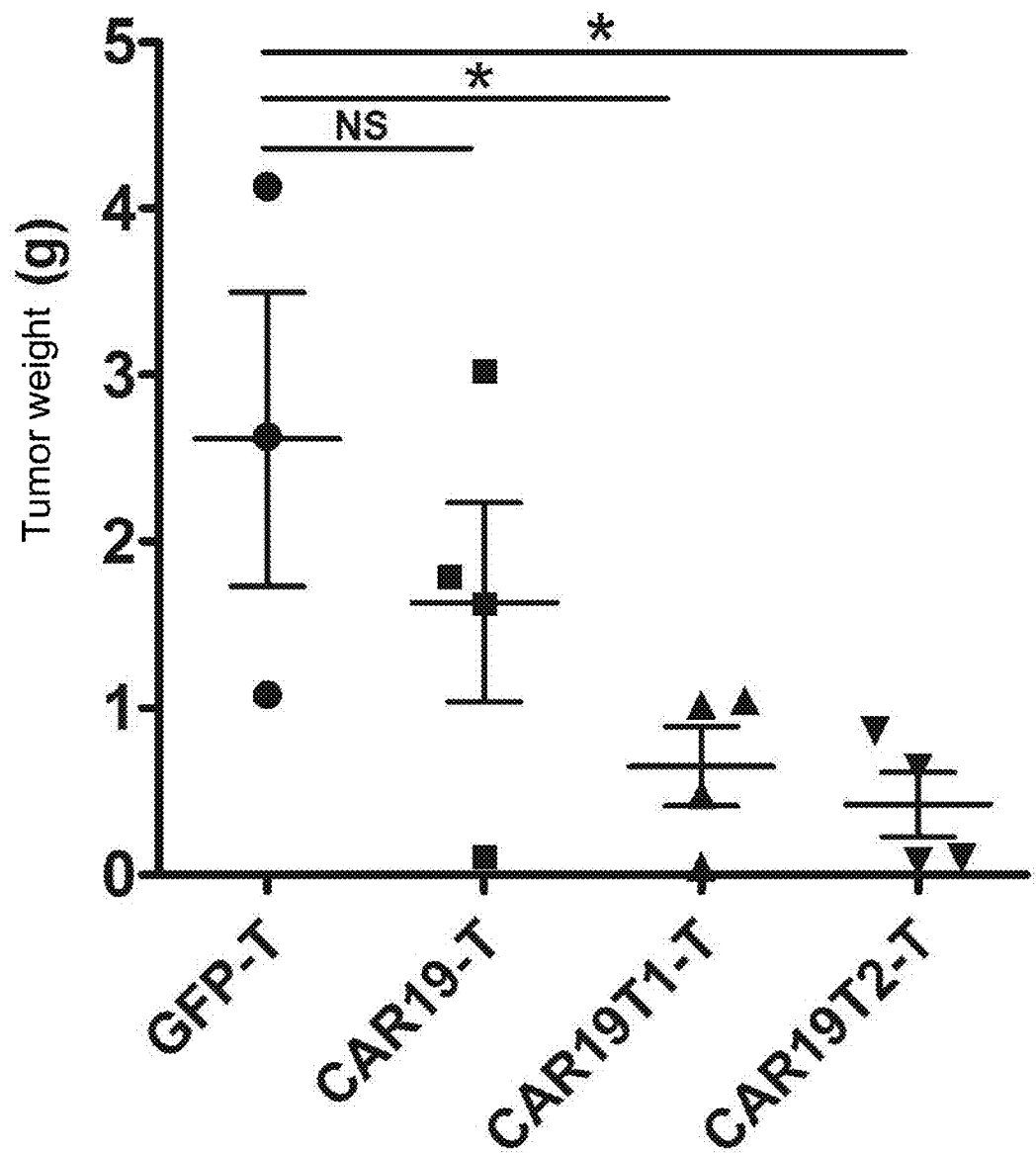
FIG. 10 shows the weight of NALM6 tumors in FIG. 9.

The results showed that, both CAR19T1 T and CAR19T2 T cells can significantly inhibit the growth of the subcutaneous NALM6 cells, and the tumor weight from the group of CAR19 T cells showed no difference compared with the group of GFP T cells (FIG. 9, 10).

On the other hand, although CAR19 T cells showed good efficacy in hematological cancers, they showed poor killing efficacy agianst subcutaneous solid tumors; however, after adding intracellular domain of TLR1 or TLR2, the killing capacity of CAR T cells against solid tumors was significantly improved.

Example 7 CARMesoT1 T Cells Showed Enhanced Efficacy Against A549 Tumor in vivo To compare CAR22, CARMesoT1 and CARMesoT2 T cells in recognizing and killing solid tumor in vivo, the identical number ($1\times10^5$) of A549 cells were subcutaneously transplanted into 12 NSI (NOD/SCID IL2rg$^{-/-}$) immunodeficient mice at the flanks, 7 days and 14 days after A549 cell transplantation (the day of transplantation of tumor cells is day 0), $2\times10^6$ T cells (three groups: CAR22 T, CARMeso T and CARMesoT1 T, four mice for each group, the proportion of positive cells as shown in FIG. 6) were intravenously injected into the NSI immunodeficient mice transplanted with A549 cells; on day 68, all the mice were euthanized for taking the tumors and weighed the same.

Figure 11:
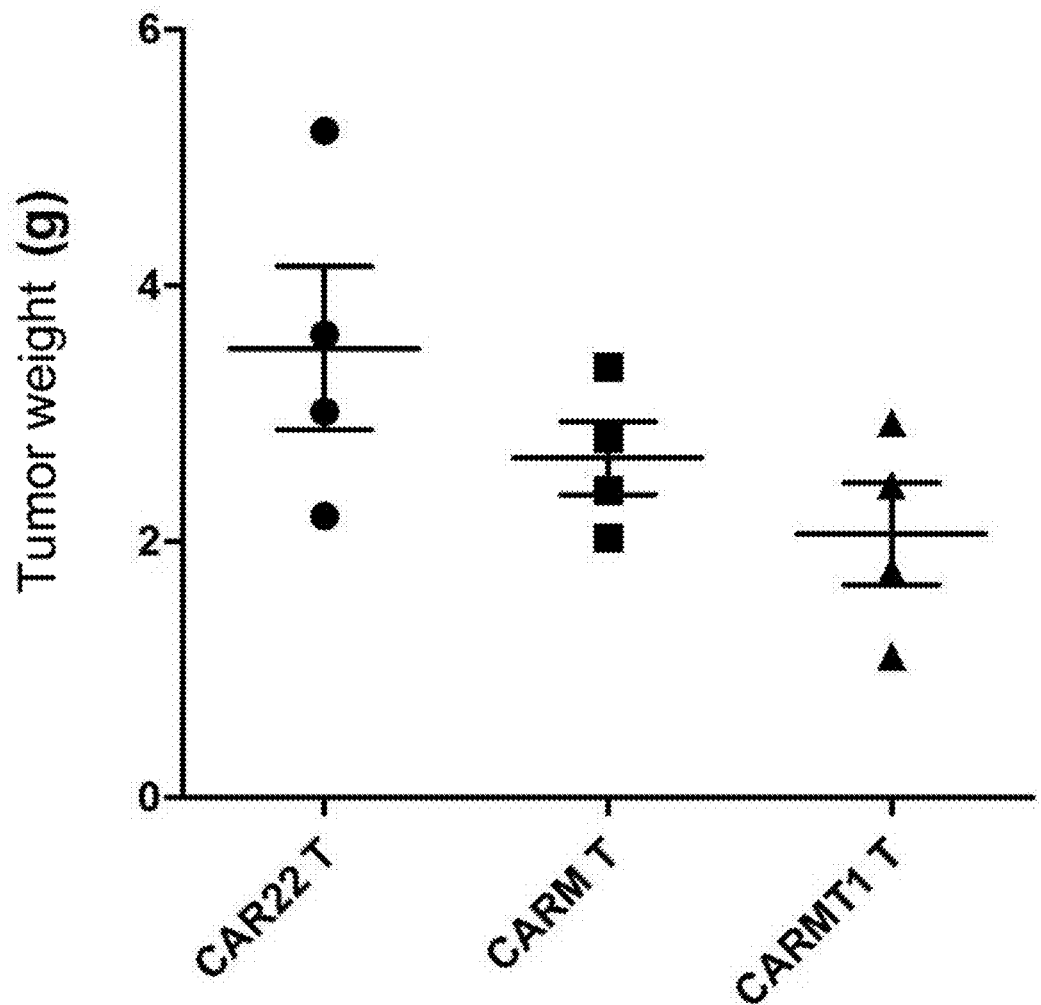
FIG. 11 shows the weight of A549 tumors in immunodeficient mice treated with CAR T cells in FIG. 6.

The results showed that, both CARMeso T and CARMesoT1 T cells can significantly inhibit the growth of the subcutaneous tumors, and compared to CARMeso T, the CARMesoT1 T cells have better effect of tumor killing in vivo (FIG. 11).

The above results comparing the effectiveness of recognizing and killing tumor of the experimental and control groups of CAR T cells indicated that both TLR1 and TLR2 signaling domains could improve the capacity of CAR T cells at killing tumors in vivo and vitro.

The applicant stated that the present invention described the product, purpose and use of the present invention by the above examples, but the present invention is not limited to the above detailed usage and use, ie. It does not mean that the present invention must rely on such detailed usage and use to implement. The one skilled in the art should be appreciated that any improvement in the present invention, the equivalent replacement of the raw materials of the product of the present invention and the addition of the auxiliary components, and the selection of specific ways, are all within the scope of protection and the scope of the disclosure of the present invention.

The invention claimed is:

1. A chimeric antigen receptor, comprising an extracellular domain capable of binding to an antigen, a transmembrane domain and an intracellular domain, wherein, the intracellular domain contains at least: a Toll-like receptor 1 intracellular signaling domain with the nucleotide sequence of SEQ ID NO. 11 and/or a Toll-like receptor 2 intracellular signaling domain with the nucleotide sequence of SEQ ID NO. 12, a CD3ζ intracellular signaling domain, and a CD28 intracellular signaling domain, wherein the antigen is a tumor associated antigen.

2. The chimeric antigen receptor according to claim 1, characterized in that, the extracellular domain capable of binding to the antigen is a single chain variable fragment of an antibody binding to the antigen.

3. The chimeric antigen receptor according to claim 1, characterized in that, the intracellular domain comprises three or more intracellular domains connected with each other; wherein the Toll-like receptor 1 and/or Toll-like receptor 2 intracellular signaling domain is arranged on the C-terminal side.

4. The chimeric antigen receptor according to claim 1, characterized in that, the chimeric receptor antigen includes, in sequence from the N-terminal side, a single chain variable region of an antibody against tumor associated antigen as the extracellular domain, the transmembrane and intracellular signaling domain of CD28 molecule, the CD3ζ intracellular signaling domain, the Toll-like receptor 1 and/or Toll-like receptor 2 intracellular signaling domain.

5. A nucleic acid encoding the chimeric antigen receptor according to claim 1.

6. A chimeric antigen receptor-expressing cell, into which the nucleic acid according to claim 5 is introduced.

7. The chimeric antigen receptor according to claim 1, characterized in that the Toll-like receptor 1 and/or Toll-like receptor 2 intracellular signaling domain is arranged on the C-terminal side of the CD3ζ intracellular signaling domain.

8. The chimeric antigen receptor according to claim 1, characterized in that the intracellular domain includes the CD28 intracellular signaling domain, the CD3ζ intracellular signaling domain, and the Toll-like receptor 1 and/or Toll-like receptor 2 intracellular signaling domain connected with each other in sequence from the N-terminal side.

9. The chimeric antigen receptor according to claim 1, characterized in that the intracellular domain includes the CD3ζ intracellular signaling domain, the Toll-like receptor 1 and/or Toll-like receptor 2 intracellular signaling domain, and the CD28 intracellular signaling domain connected with each other in sequence from the N-terminal side.

10. The chimeric antigen receptor according to claim 4, characterized in that the tumor associated antigen is CD19 or Mesothelin antigen.

11. The chimeric antigen receptor according to claim 6, wherein the cell is a T cell or a cell population containing T cells.

12. A method for treating a tumor, comprising the administration of a chimeric antigen receptor-expressing cell, into which a nucleic acid encoding the chimeric antigen receptor according to claim 1 is introduced.

13. The method according to claim 12, wherein the tumor is hematological tumor or solid tumor.

* * * * *